US008224675B2

(12) United States Patent
Thorne et al.

(10) Patent No.: US 8,224,675 B2
(45) Date of Patent: Jul. 17, 2012

(54) METHOD AND SYSTEM FOR INSURANCE COMPANIES CONTRACTING WITH AND PAYING MEDICAL IMAGE READING PROFESSIONALS IN A NETWORK

(75) Inventors: Curtis J. Thorne, Nashville, TN (US); Gregg Phillip Allen, Franklin, TN (US)

(73) Assignee: Premerus, LLC, Franklin, TN (US)

( * ) Notice: Subject to any disclaimer, the term of this patent is extended or adjusted under 35 U.S.C. 154(b) by 512 days.

(21) Appl. No.: 12/365,815

(22) Filed: Feb. 4, 2009

(65) Prior Publication Data

US 2009/0204445 A1 Aug. 13, 2009

Related U.S. Application Data

(60) Provisional application No. 61/065,085, filed on Feb. 8, 2008, provisional application No. 61/065,055, filed on Feb. 8, 2008, provisional application No. 61/065,062, filed on Feb. 8, 2008, provisional application No. 61/065,061, filed on Feb. 8, 2008.

(51) Int. Cl.
*G06Q 10/00* (2012.01)
(52) U.S. Cl. ............................ 705/4; 600/300; 600/301
(58) Field of Classification Search .................. 705/2–3; 600/300–301
See application file for complete search history.

(56) References Cited

U.S. PATENT DOCUMENTS

| | | | |
|---|---|---|---|
| 7,765,109 B2* | 7/2010 | Gutman et al. .................. 705/2 |
| 7,831,445 B2 | 11/2010 | Reiner | |
| 2002/0010395 A1 | 1/2002 | Stawder | |
| 2005/0187787 A1 | 8/2005 | Tomlinson, Jr. et al. | |
| 2005/0256743 A1 | 11/2005 | Dale | |
| 2006/0005347 A1* | 1/2006 | Griffin et al. .................. 15/339 |
| 2006/0106640 A1 | 5/2006 | Deline | |
| 2006/0122865 A1 | 6/2006 | Preiss et al. | |
| 2006/0173663 A1 | 8/2006 | Langheier et al. | |
| 2006/0195339 A1 | 8/2006 | Backhaus et al. | |
| 2007/0011024 A1 | 1/2007 | Dale et al. | |
| 2007/0136355 A1 | 6/2007 | Haider | |
| 2007/0232868 A1* | 10/2007 | Reiner .......................... 600/300 |
| 2007/0250352 A1 | 10/2007 | Tawil | |

(Continued)

FOREIGN PATENT DOCUMENTS

WO WO2006057953 1/2006

(Continued)

OTHER PUBLICATIONS

Woodard et al, "Performance assessment for radiologists interpreting screening mammograph," Jul. 17, 2006, Wiley. InterScience, 26:1532-1551.

(Continued)

*Primary Examiner* — Vivek Koppikar
(74) *Attorney, Agent, or Firm* — SNR Denton US, LLP (57) ABSTRACT

A system and method for insurance companies contracting with and paying medical image reading professionals in a medical image reading professionals network. The network may be independent of a medical facility and be arranged to have each of the medical image reading professionals may be an expert in reading medical images of particular anatomical regions. The insurance companies may have lower overall costs by contracting with the medical image reading professionals who are experts in reading medical images of anatomical regions, modalities, and medical conditions as misdiagnoses are reduced due to proficiency of the medical image reading professionals.

15 Claims, 7 Drawing Sheets

U.S. PATENT DOCUMENTS

| | | |
|---|---|---|
| 2008/0004904 A1 | 1/2008 | Tran |
| 2008/0306760 A1 | 12/2008 | Minnigh et al. |
| 2009/0094058 A1 | 4/2009 | Reiner |
| 2009/0132285 A1 | 5/2009 | Jakobovits |

FOREIGN PATENT DOCUMENTS

| | | |
|---|---|---|
| WO | WO2007062523 | 7/2007 |
| WO | WO2007089686 A2 | 8/2007 |

OTHER PUBLICATIONS

Non-Final Rejection mailed Jun. 6, 2011 for U.S. Appl. No. 12/365,787.
Response to Non-Final Rejection filed Sep. 6, 2011 U.S. Appl. No. 12/365,787.
Final Rejection mailed Nov. 28, 2011 for U.S. Appl. No. 12/365,787.
Response to Final Rejections mailed Jan. 27, 2012 for U.S. Appl. No. 12/365,787.
Notice of Allowance mailed Mar. 28, 2011 for U.S. Appl. No. 12/365,796.
Amendment after Allowance filed Jun. 23, 2011 for U.S. Appl. No. 12/365,796.
Response to amendment after Notice of Allowance mailed Jul. 28, 2011 for U.S. Appl. No. 12/365,796.
Request of Continuted Prosecution Aug. 3, 2011 for U.S. Appl. No. 12/365,796.
Supplemental Notice of Allowance Aug. 24, 2011 for U.S. Appl. No. 12/365,796.
Non-Final Rejections mailed Aug. 12, 2011 for U.S. Appl. No. 12/365,824.
Amendment after Non-Final Rejection filed Nov. 14, 2011 for U.S. Appl. No. 12/365,824.
Final Rejection mailed Dec. 30, 2011 U.S. Appl. No. 12/365,824.
Restriction Requirement mailed Dec. 28, 2011 U.S. Appl. No. 13/167,579.
Response to Restriction Requirement Jan. 26, 2012 U.S. Appl. 13/167,579.

* cited by examiner

METHOD AND SYSTEM FOR INSURANCE COMPANIES CONTRACTING WITH AND PAYING MEDICAL IMAGE READING PROFESSIONALS IN A NETWORK

CROSS-REFERENCE TO RELATED APPLICATIONS

This application claims priority to the following U.S. Provisional Patent Applications: Ser. No. 61,065,085 filed on Feb. 8, 2008; 61/065,055 filed on Feb. 8, 2008; 61/065,062 filed on Feb. 8, 2008; and 61/065,061 filed on Feb. 8, 2008, the entire teachings of which are herein incorporated by reference.

BACKGROUND

The practice of medicine has greatly advanced as evidenced by patients being treated with previously incurable diseases, such as cancer. One reason, among many, for the advancement of medicine is a result of improvement of medical imaging technology. Medical images may include many different types of images of the human body, including radiological images, CAT scan images, endoscopic images, magnetic resonance images, etc. Through the use of medical imaging technology, medical professionals are able to see images of internal organs, for example, of patients to help diagnose medical conditions of the patients. Medical imaging allows for diseases, such as breast cancer, to be diagnosed in early stages, which greatly improves chances of recovery. While medical imaging technology has significantly improved medical care, because of the nature of creating and interpreting medical images, radiological or other imaging techniques, inaccuracies in the imaging and interpretation processes of the medical images may result. Because of the inaccuracies in the imaging and interpretation processes, patient medical conditions are often misdiagnosed.

Misdiagnosis of a medical condition, such as a disease, may come in the form of false positives, false negatives, and equivocal diagnoses. A false positive is a detection of a disease that does not exist. A false negative is a failure to detect a disease that is present in a patient. An equivocal diagnosis is a statement that a definitive diagnosis cannot be made based on the information available (e.g., "cancer cannot be ruled out"). Each of these misdiagnoses results in higher costs of treatment, additional suffering to patients, and additional burden on the healthcare system as a whole. It has been estimated that frequency of misdiagnosis of radiological imaging interpretations is as high as 30%. And, given that it has been estimated that 40% to 60% of total healthcare spend is influenced by radiological imaging and interpretations therefrom, misdiagnoses results from misinterpretation of medical imaging has a large impact on the healthcare system.

An example of the effects of a misdiagnosis is as follows. A medical image reading professional identifies a spot on a lung. The lung spot may be any of a number of different medical conditions, including a benign solitary pulmonary nodule, small cell lung carcinoma, non-small cell lung carcinoma, or any number of other medical conditions. If the medical image reading professional determines that the lung spot is a benign solitary pulmonary nodule, but also denotes that "cancer cannot be ruled out," a treating medical professional is compelled to perform additional testing, a biopsy of the lung spot, and possibly surgery to remove the lung spot to avoid a malpractice claim. The cost for each of these additional diagnostic treatments can be very high from financial, patient anxiety and pain, and medical system resource perspectives. If it turns out that after the additional diagnostic treatments that the patient had a benign, solitary pulmonary nodule that could have been identified by the medical image reading professional at the initial medial image reading, all of the additional diagnostic treatments would have been avoided.

Although medical professionals are considered to be highly regarded, and justifiably so in most cases, medical professionals are not all trained in the same manner or have the same level of proficiency as one another. As in all professions, some medical professionals may have better education, training, or any other differentiator than other medical professionals. For example, one medical image reading professional may have better eyesight or cognitive reasoning skills than another and, therefore, be better at determining a correct or more accurate diagnosis than another with worse eyesight or cognitive reasoning skills.

Medical image reading professionals are affiliated with medical facilities, such as hospitals, clinics, medical offices, imaging centers, or other medical facilities. As understood in the art, medical insurance companies or payors contract with medical facilities to pay the medical facilities for services rendered by medical professionals at the medical facilities. For example, when a patient visits a medical facility, the patient receives services from one or more medical professionals, including medical image reading professionals. Medical image reading professionals often assist treating physicians by reading medical images and diagnosing medical conditions so that treating physicians may create treatment plans or perform additional testing. Because medical facilities are typically general in treating medical conditions and cannot afford to have a large medical image reading professional staff, each medical image reading professional tends to become generalized and read medical images of a wide variety of anatomical regions. If a treatment plan is approved by a medical insurance company that is a provider of the patient, the medical insurance company pays the medical facility or medical professionals who participated in treating the patient. One problem that exists is that, as described above, not all medical professionals, including medical image reading professionals, have the same level of proficiency and insurance companies who contract with a patient are responsible for paying medical professionals with varying degrees of proficiency. And, if a patient is diagnosed or treated incorrectly, the medical insurance company will pay more for the diagnostic procedures and treatment then if the patient was correctly diagnosed and treated.

SUMMARY

To overcome the problems of insurance companies having to pay for medical professionals with varying degrees of proficiency, which leads to higher medical costs, the principles of the present invention provide for insurance companies to contract with medical image reading professionals who participate in a network of medical image reading professionals. The medical image reading professionals in the network may be screened by a network manager such that each medical image reading professional is determined to be proficient. Furthermore, each medical image reading professional may be an expert in that he or she reads a particular modality of imaging for particular anatomical regions of patients and some or all related diagnoses medical conditions of those anatomical regions. By being an expert, each of the medical image reading professionals is likely to be more proficient than a general medical image reading professional, thereby providing higher levels of accuracy and reducing overall healthcare costs for insurance companies, patients, and the healthcare system as a whole. Rather than being affiliated with a medical facility, the medical image reading professionals in the network may be affiliated with a medical image reading professional network manager. In one embodiment, the medical image reading professional network manager operates to manage medical images workflow being distributed to the medical image reading professionals based on demonstrated competency specific to the needs of patients and all other relevant matters, such as availability and licensing. Thus, insurance companies that contract with the medical image reading professionals directly or via the medical image reading professional network manager is able to reduce costs due to the expert medical image reading professionals providing higher accuracy than general medical image reading professionals who are affiliated with medical facilities.

One embodiment of a system and method for insurance companies contracting with and paying medical image reading professionals in a medical image reading professionals network may include the network of medical image reading professionals being independent of a medical facility. Each of the medical image reading professionals may be an expert in reading medical images of particular anatomical regions. In one embodiment, the medical image reading professionals may further or alternatively be experts in imaging modalities and/or reading medical conditions. The insurance companies may have lower overall costs by contracting with the medical image reading professionals who are experts in reading medical images of anatomical regions as misdiagnoses are reduced due to proficiency of the medical image reading professionals.

One embodiment of a system for paying medical image reading professionals may include a first module configured to recognize a network of medical image reading professionals who interpret medical information of patients to qualify for medical insurance payment reimbursement. Each medical image reading professional in the network may have at least one rating parameter associated therewith indicative of outcome of patients who were treated based on assessments of medical conditions by a respective medical image reading professional. A second module may be in communication with the first module, and be configured process insurance payment requests for the medical image reading professionals.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF DRAWINGS

Figure 1:
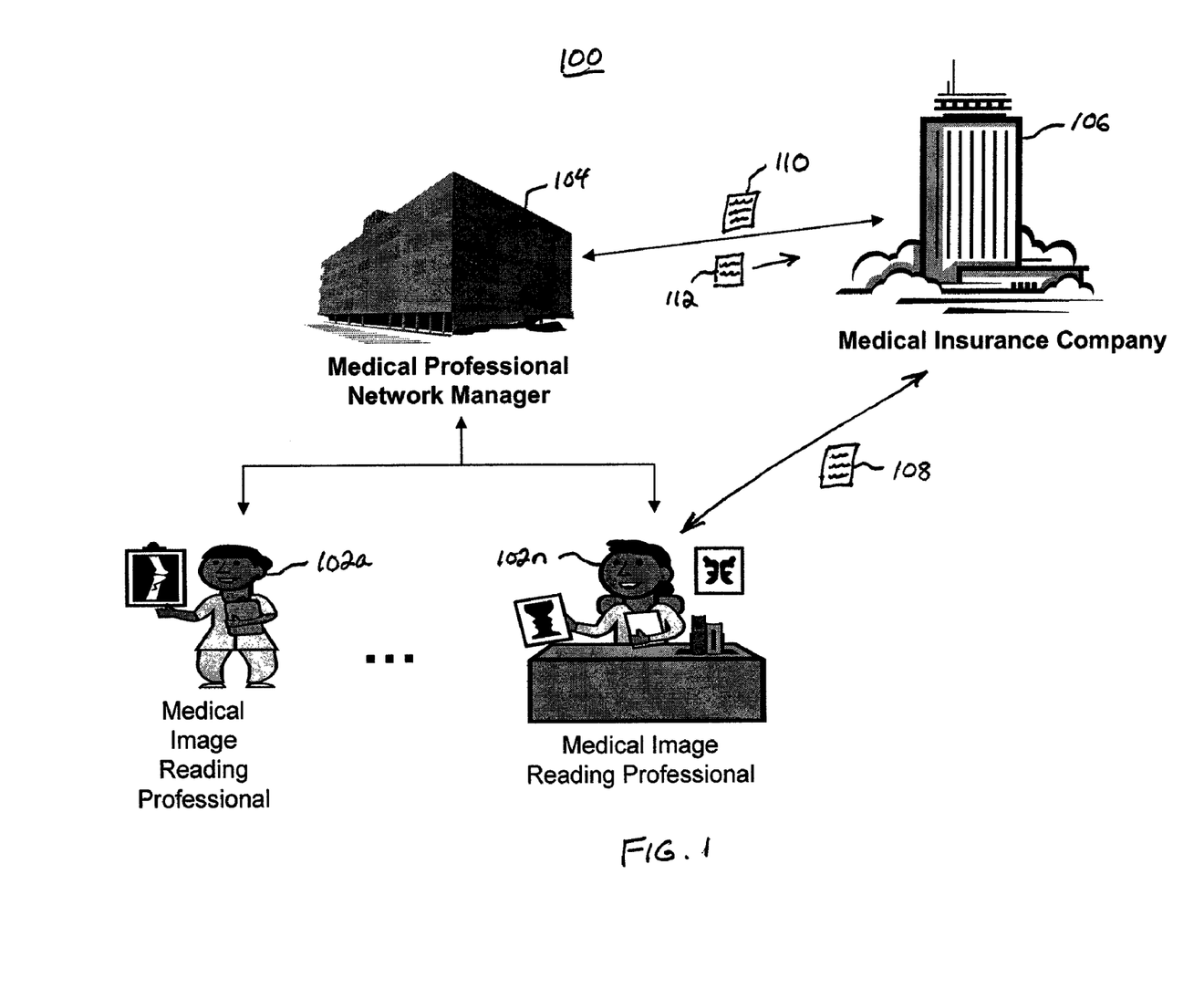
FIG. 1 is an illustration of a network of medical image reading professionals.

FIG. 1 is an illustration of a network 100 of medical image reading professionals 102a-102n (collectively 102). The medical image reading professionals 102 may be radiologists, medical doctors, or any other medical professional who reads and diagnoses medical conditions, such as diseases, of patients by reading medical images. A medical professional network manager 104 may create the medical image reading professional network 100 using a variety of techniques. In one embodiment, the medical professional network manager 104 establishes predetermined acceptance criteria for the medical image reading professionals 102 who apply to participate in the medical image reading professional network 100. The predetermined acceptance criteria may be a minimum number of medical images of a specific modality for a defined anatomical region and/or clinical condition read by a medical image reading professional on an annual or other time duration basis, a certain number of years of work experience, or other predetermined acceptance criteria that the medical professional network manager 104 may consider relevant as to predicting proficiency of a medical image reading professional. Alternative or combinations of predetermined criteria may be utilized in creating the medical image reading professional network. A modality is considered a particular technique or technology used to capture an image of an anatomical region or condition. By using predetermined acceptance criteria, the medical image reading professional network may be established with medical image reading professionals 102 meeting at least one criterion for having a certain level of competence for accurately diagnosing medical conditions of patients. More particularly, each medical image reading professional may be experts in reading medical images for a particular anatomical region and/or clinical condition, as described below.

A medical insurance company 106 may form a contract 108 with each of the medical image reading professionals 102 of the medical image reading professionals network 100. Alternatively, the medical insurance company 106 may form a group contract 110 with the medical professional network manager 104 that covers each of the medical image reading professionals 102. For the purposes of this description, a contract with the medical professional network manager 104 and the medical insurance company 106 is, in effect, a contract with the medical image reading professionals 102. The medical insurance company 106 derives a benefit from contracting with the medical image reading professionals 102 who are experts in reading medical images of particular respective anatomical regions, modalities, and/or clinical conditions as each of the medical image reading professionals 102 are proficient in their abilities, which drives down medical insurance claims as a whole due to fewer misdiagnoses occurring.

As understood in the art, there are many different types of medical images. It should also be understood that the most proficient medical image reading professionals tend to be experts in reading certain types of medical images. Proficiency of medical image reading professionals can be determined, where proficiency is the ability for a medical image reading professional to accurately interpret information related to medical images in order to diagnose a medical condition. Further, characteristics of proficient reading professionals can be used to construct predictive models for identifying other proficient reading professionals. In other words, medical image reading professionals who are highly skilled may have historical attributes to their careers or personal lives that caused them to become highly skilled. Being highly skilled may mean that a medical image reading professional is in the top 3% or 5% of all medical image reading professionals who read medical images of the same modality, anatomical regions, and/or medical conditions. The historical attributes of a medical image reading professional may include particular schools, professors, supervisors, mentors, curriculum, grade point averages, sports participation, or any other attribute, either directly or indirectly related to medical training, physical characteristics (e.g., eyesight), or mental skill (e.g., logical reasoning, obsessive compulsive, or "A" type personality). The historical attributes may be collected and stored in one or more databases. A searching or mining software algorithm executed on a computer may be configured to access and search the database(s) to identify historical data of highly skilled medical image reading professionals that are related to or match experts for reading particular modalities, anatomical regions, and/or conditions, thereby enabling a medical image reading professional network manager to better "scout" medical image reading professionals who are or have the potential to become highly skilled.

In contracting either directly with the medical professional network manager 104 or each medical image reading professional 102 of the network of medical image reading professionals, the medical insurance company 106 may have an agreement with the medical professional network manager 104 to provide information about medical images of patients that are being read by the medical image reading professionals 102, including information that describes anatomical regions captured in the medical images. Furthermore, the agreement between the medical insurance company and medical professional network manager may have the medical professional network manager 104 provide information describing specific expertise of each medical image reading professional who reads the medical images, thereby providing a verification that each set of medical images is being read by an appropriate expert. By the medical image reading professional information 112 being provided to the medical insurance company 106, the medical insurance company 106 is ensured that the appropriate medical image reading professional 102 is used to perform readings of medical images so as to minimize misdiagnoses and lowering payment costs for the medical insurance company 106.

Figure 2:
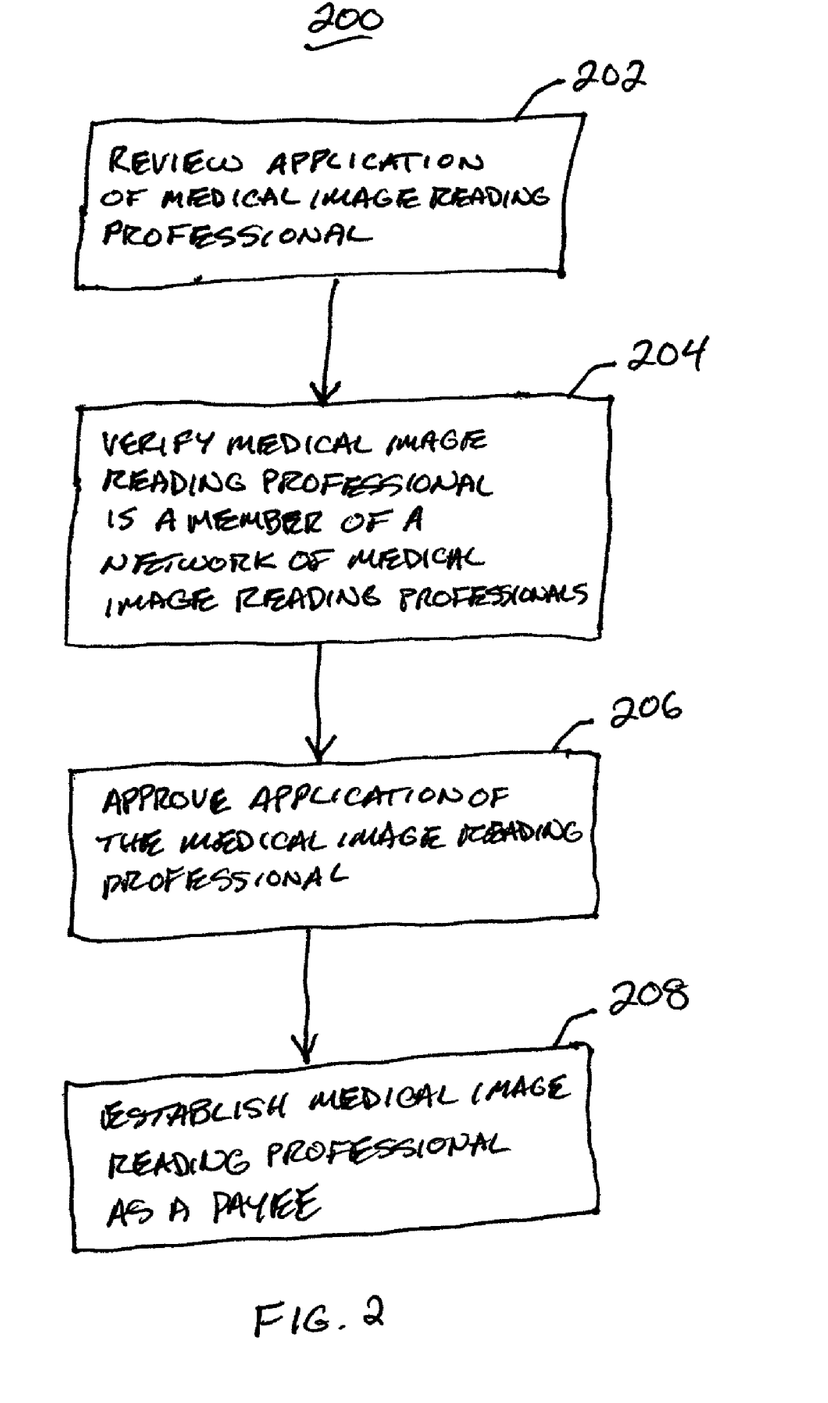
FIG. 2 is a flow diagram of an exemplary process for an insurance company to contract with medical image reading professionals.

FIG. 2 is a flow diagram of an exemplary process 200 for an insurance company to contract with medical image reading professionals. The process 200 starts at step 202, where an application of a medical image reading professional is reviewed by an insurance company. In operation, the medical image reading professional receives medical information including medical images from a medical professional network manager to perform his or her medical image reading duties. Furthermore, the medical image reading professional is one who has qualified to participate in a network of medical image reading professionals that the medical professional network manager manages. The medical professional network manager may be an independent entity that is not associated with a medical facility, such as a hospital. By being independent, the medical professional network manager may utilize medical image reading professionals who are independent and associated with medical facilities. For example, the medical image reading professionals may be teleradiologists. In qualifying to participate in a network of medical professionals, the medical image reading professional may have sufficient credentials to sit for an examination, whereby the medical image reading professional may read test medical images showing patients with certain medical conditions to diagnosis the medical conditions presented in the medical images. If the medical image reading professional scores above a certain level, such as 80%, then the medical image reading professional may be admitted to participate in the network of medical image reading professionals.

At step 204, a verification that the medical image reading professional is a member of a network of medical image reading professionals may be performed. The verification may include contacting the medical professional network manager to determine that the medical image reading professional is, in fact, a member of the network. Furthermore, information associated with the medical image reading professional may be provided to identify a particular expertise of anatomical regions of which the medical image reading professional is an expert. At step 206, an application of the medical image reading professional may be approved by the insurance company. The medical image reading professional may be established as a payee by the medical insurance company so that the medical image reading professional may be paid by the insurance company for performing readings and diagnoses of medical images. It should be understood that the medical insurance company may contract with the medical professional network manager who, in turn, has the medical image reading professional fill out the medical insurance forms for coverage.

Figure 3:
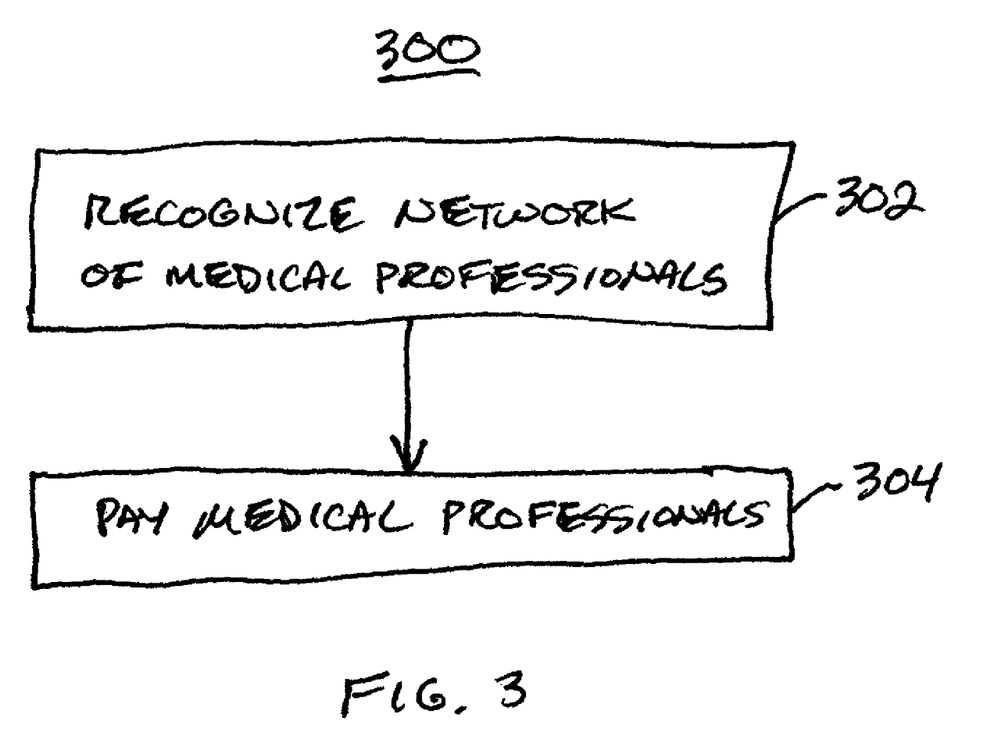
FIG. 3 is a flow diagram of an exemplary process for paying medical image reading professionals.

FIG. 3 is a flow diagram of an exemplary process 300 for paying medical professionals. The process 300 may include recognizing a network of medical professionals who interpret medical information of patients to qualify for medical insurance payment reimbursement at step 302. Each medical professional in the network may have at least one rating parameter associated therewith indicative of outcome of patients who were treated based on assessment of a medical condition by the respective medical professionals. The rating parameter(s) may be formulated through monitoring of medical insurance claims, medical treatment plans, or otherwise, as described in co-filed U.S. patent application entitled, "System and Method for Managing Medical Professionals," which is incorporated herein by reference in its entirety. At step 304, the medical professionals in the network who treat the patients are paid. The process 300 may further include paying referring medical professionals who refer the patients to a medical professional in the network of medical professionals. In addition, the referring medical professionals may be paid different from referring medical professionals who refer the patients to a medical professional not in the network of medical professionals. The recognized medical professionals may be medical image reading professionals.

Figure 4:
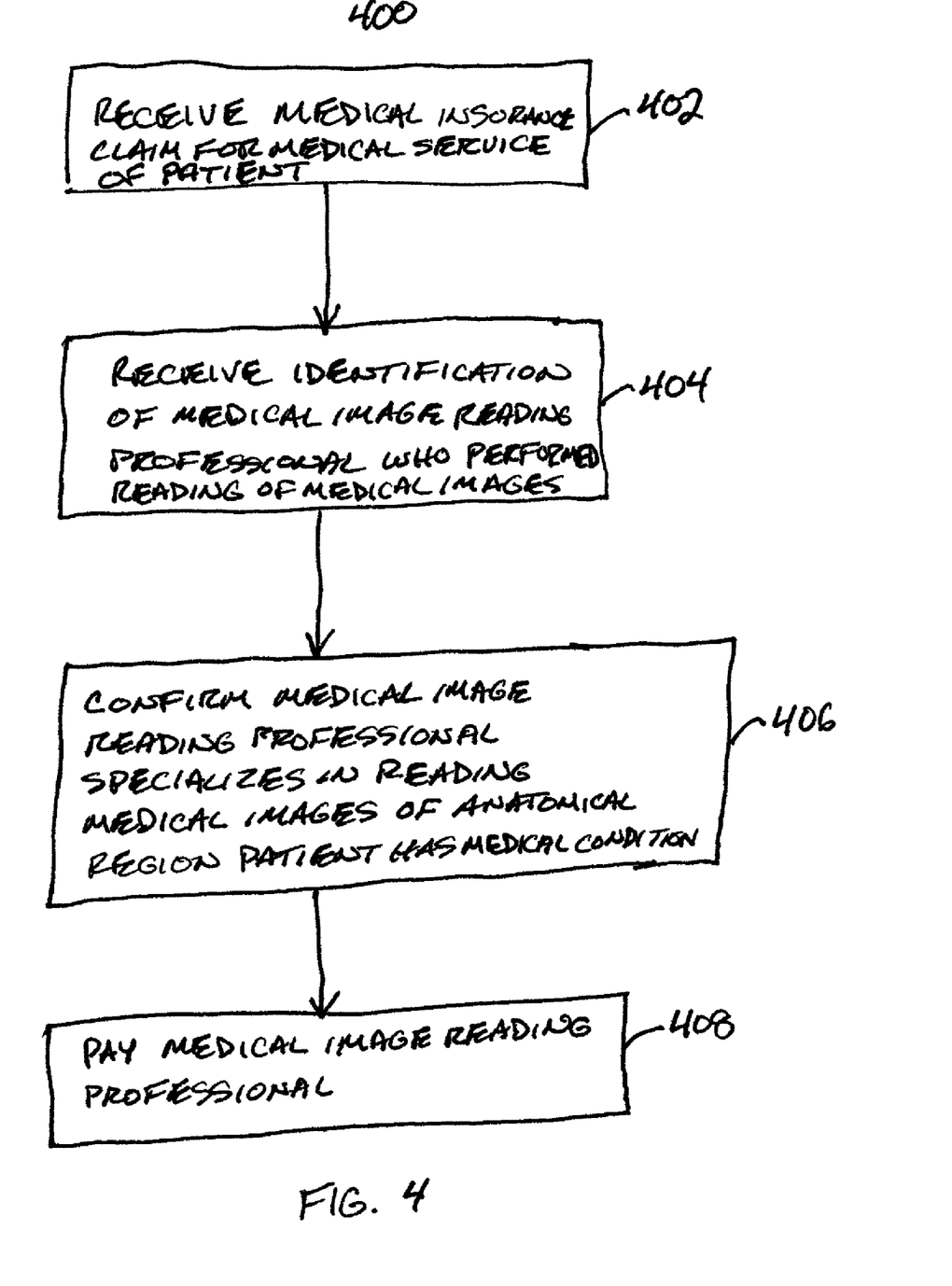
FIG. 4 is a flow diagram of an exemplary process for paying medical image reading professionals for performing image reading services

FIG. 4 is a flow diagram of an exemplary process 400 for paying medical image reading professionals for performing image reading services. The process 400 may start at step 402, where a medical insurance claim for medical services having been performed on a patient with a medical condition of an anatomical region may be received. The medical insurance claim may indicate medical image reading services having been rendered by a medical image reading professional. An identification of a medical image reading professional who performed the medical image reading services may be received. The identification may include license number, name, code, or any other indicia. At step 406, a confirmation that the medical image reading professional is an expert in reading medical images of the anatomical region of which the patient has a medical condition may be performed. By confirming that the medical image reading professional actually read the medical images, the medical insurance company may be comforted in that it was likely to have been correctly read and a correct diagnosis resulted from the medical image reading professional performing the reading. At step 408, the medical image reading professional may be paid for performing the medical image reading services.

In one embodiment, the medical image reading professional may be in a network of medical image reading professionals that is independent of a medical facility. Furthermore, the process 400 may include receiving a medical claim for medical service from a treating physician, where the treating physician referred the patient to a medical image reading professional outside the network, and paying the treating physician a different amount than had the treating physician referred the patient to the medical image reading professional in the network of medical image reading professionals.

Figure 5:
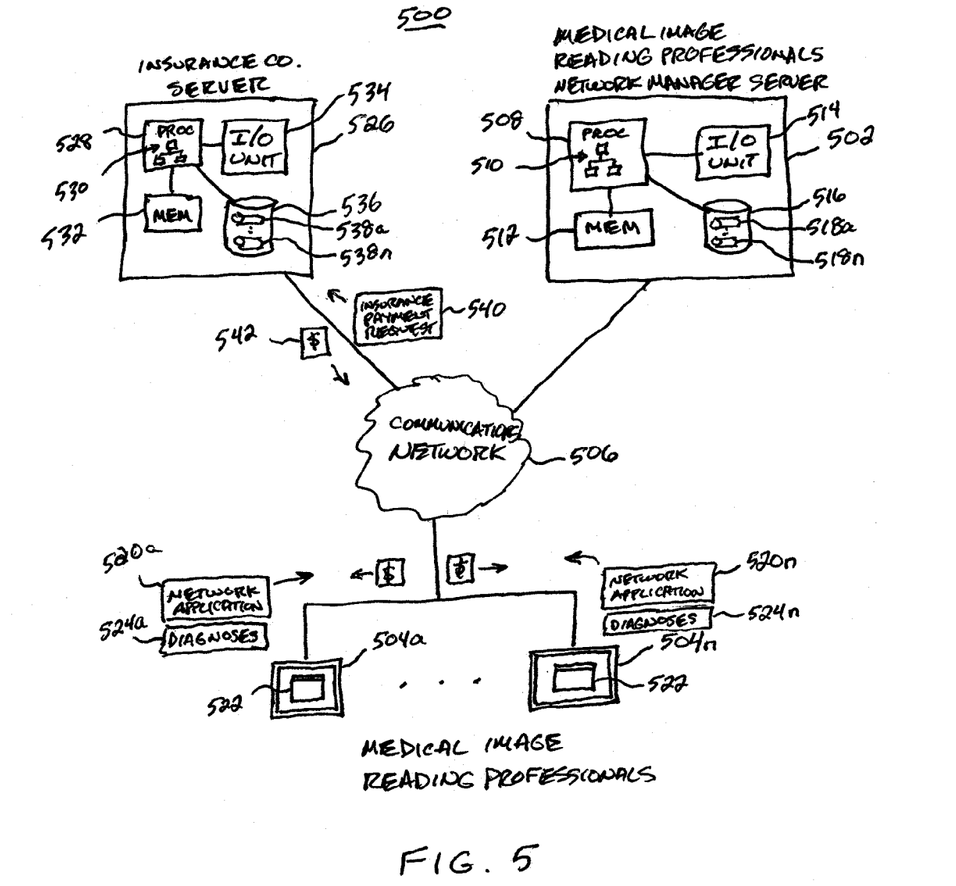
FIG. 5 is an illustration of an illustrative network environment in which medical image reading professionals may apply for a position in a medical image reading professionals network.

FIG. 5 is an illustration of an illustrative network environment 500 in which medical image reading professionals may apply for a position in a medical image reading professionals network, which may be a group of medical image reading professionals that are coordinated by a medical image reading professionals network manager. The network environment 500 may include a medical image reading professionals network manager server 502 that may be configured to manage information and communications with medical image reading professionals via computers 504a-504n (collectively 504) in the medical image reading professionals network via communications network 506. In one embodiment, the communications network 506 is the Internet. However, the network 506 may be any communications network that data, such as medical image data, may be communicated and viewed on the computers 504.

The medical image reading professionals network manager server 502 may include a processing unit 508 that executes software 510. The server 502 may further include a memory 512, input/output (I/O) unit 514, and storage unit 516. The storage unit 516 may be configured to store one or more data repositories 518a-518n (collectively 518). In one embodiment, the data repositories are databases. The software may be configured to manage distribution of medical image reading professionals network information, such as applications for medical image reading professionals to join the medical image reading professionals network. The processing unit 508 may communicate information over the communications network 506 via the I/O unit 514.

The data repositories 518 may be configured to store information associated with managing the medical image reading professionals network, medical images, diagnoses, patients, and any other information that may be helpful to medical image reading professionals, doctors, and patients. The software 510 may further be configured to enable the medical image reading professionals using computers 504 to access a website that enables the medical image reading professionals to download and fill out network applications 520a-520n to join the network of medical image reading professionals. Data that is entered into the network applications 520 may be communicated via the communications network 506 to the server 502 for storage in the data repositories 518, as provided in TABLE I. In addition, once a medical image reading professional has been working in the network for a period of time, a rating may be applied to the medical image reading professional based on outcome of patients who were treated from the diagnoses of the medical image reading professional.

TABLE I

| First Name | Last Name | Address | Board Cert. No. | Anatomical Expertise | Readings per Year | Modality | Conditions | Rating |
|---|---|---|---|---|---|---|---|---|
| Mark | Sullivan | 5790 Albo Rd Brookline, MA | MA748421 | Knee | 5500 | MR | ALL | 9.4 |
| Lisa | Shain | 5250 Oak Ln. Dallas, TX | TX748212 | Heart | 4800 | CTA | Angio | 9.6 |
| ... | ... | ... | ... | ... | ... | ... | ... | ... |

If the medical image reading professional network manager decides that the medical image reading professional who submitted a network application qualifies to be in the medical image reading professional network, then the medical image reading professional may have access to other information stored in the data repositories 518 and be included for distribution of medical images for specific anatomical regions, modalities, and/or conditions in which the medical image reading professional is an expert. The data repositories 518 may store medical images and enable medical image reading professionals in the medical image reading professionals network to access the medical images via their computers 504 for display in a graphical user interface 522. In one embodiment, the graphical user interface 522 is a website that is operated by the server 502. In response to reading medical images, the medical image reading professionals may communicate diagnoses 524a-524n (collectively 524) to the server 502 for storage in one of the data repositories 518. Medical professionals (not shown) may access the diagnoses 524 made by the medical image reading professionals via the communications network 506 in order to determine treatment plans for the patients.

Because the medical image reading professionals are members of the medical image reading professionals network that has been recognized by insurance, the insurance companies are willing to pay the medical image reading professional either directly or via the medical image reading professional network manager. Insurance companies may also be provided access to or be in communication with the server 502 to verify background and status of medical image reading professionals.

An insurance company server 526 may include a processing unit 528 that executes software 530. The software 530 may be configured to process information received via the communications network 506. The server 526 may further include a memory 532 for storing data and software, input/output unit 534 for communicating data over the communications network 506, and storage unit 536. The storage unit 536 may be configured to store one or more data repositories 538a-538n (collectively 538) that store information of patients, medical professionals, medical image reading professionals, insurance policies, and so forth. In operation, the server 526 may be configured to receive insurance payment requests 540 via the communications network 506. In one embodiment, the insurance payment request communications 540 may be from the medical image reading professionals network manager server 502 or from a medical image reading professionals network manager who, in response to receiving diagnoses 524 from medical image reading professionals in response to reading medical images of patients, may communicate the insurance payment requests 540.

The software 530 being executed by the processor 528 on the insurance company server 526 may process the insurance payment requests 540 and authorize payment 542 to be issued to the medical image reading professionals network manager or medical image reading professional. It should be understood that rather than the server 526 authorizing the payment 542, that an individual at the insurance company may view the insurance payment requests 540 and issue payments for the diagnoses 524 being performed by the medical image reading professionals in a more conventional manner, such as by writing a check or performing a direct deposit via a bank. In one embodiment, the software 530 may be configured to provide for a graphical user interface, such as a webpage, that the medical image reading professionals network or medical image reading professionals may access to submit insurance payment requests 540.

Figure 6:
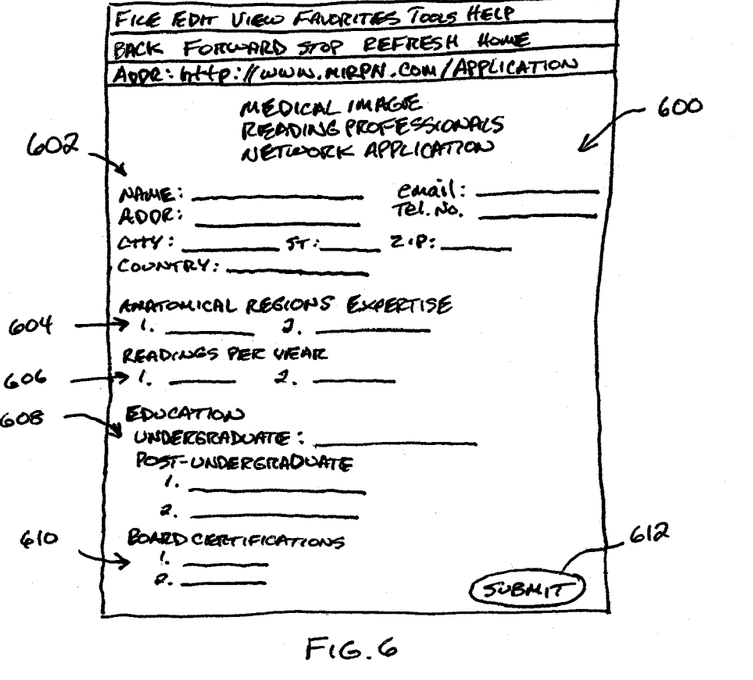
FIG. 6 is an illustration of an illustrative graphical user interface in the form of a webpage configured to enable medical image reading professionals to submit an application to join a medical image reading professionals network.

FIG. 6 is an illustration of an illustrative graphical user interface in the form of a webpage 600 that is used for a medical image reading professional to submit an application to join a medical image reading professional network. The webpage 600 may include an identification section 602, anatomical regions expertise entry fields 604, readings per year entry fields 606, education entry fields 608, and board certifications entry fields 610. In one embodiment, the webpage 600 may be hosted by server 502 (FIG. 5) and accessed by medical image reading professionals using computers 504 to join the medical image reading professionals network. The anatomical regions expertise and readings per year entry fields 604 and 606 enable the medical image reading professionals network manager to determine what anatomical regions the medical image reading professionals consider themselves as being experts. The total number of readings per year on each of the particular anatomical regions may assist the medical image reading professionals network manager to determine whether the medical image reading professionals are, in fact, experts as desired by the medical image reading professionals network and insurance companies. Once the medical image reading professional has entered his or her information in the application of the webpage 600, the medical image reading professional may select the "submit" softbutton 612 to submit the information to the medical image reading professionals network manager.

In an alternative embodiment, the medical image reading professionals network application may be an electronic document, such as a PDF document, that the medical image reading professionals may download to fill-out and e-mail, scan, fax, or otherwise return to the medical image reading professionals network manager. The network manager may utilize the information provided by the medical image reading professionals by managing medical image reading professionals and medical image reading operations performed by the medical image reading professionals network.

Figure 7A:
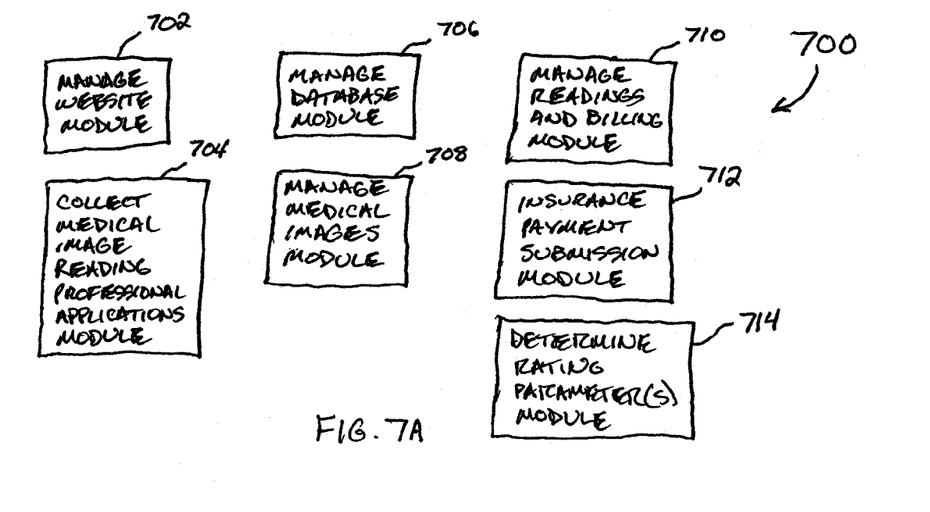
FIG. 7A is a block diagram of an illustrative set of modules configured to process information to enable a medical image reading professionals network manager to manage its network of medical image reading professionals.

FIG. 7A is a block diagram of an illustrative set of modules 700 configured to process information to enable a medical image reading professionals network manager to manage its network of medical image reading professionals. The modules 700 may be software modules that are part of the software 510 (FIG. 5) being executed by the processing unit 508 of the server 502. The modules 700 may be configured to enable the medical image reading professionals network manager to manage information collected from the medical image reading professional, such as an application to join the medical image reading professionals network and diagnoses generated by the medical image reading professionals. Information, such as medical images and preliminary diagnoses or other information collected from medical professionals (e.g., treating physicians), may be delivered to the medical image reading professionals.

The modules 700 may include a managed website module 702 that is configured to manage a website of the medical image reading professionals network manager that enables the medical image reading professionals to access and submit an application to join the network, access medical images, and provide diagnoses in response to reading the medical images. The managed website module 702 may also manage access to the website, such as limiting access to only medical image reading professionals who are part of the medical image reading professionals network by using user names and passwords, as understood in the art. To comply with state and federal regulations, the managed website module 702 may be configured to comply with patient healthcare information rules and regulations, such as the Health Insurance Portability Accountability Act (HIPAA), as understood in the art.

A collect medical image reading professionals applications module 704 may be configured to enable medical image reading professionals who desire to become part of the medical image reading professionals network to download an application (see FIG. 6) and receive data entered by medical image reading professionals who apply to become part of the medical image reading professionals network. The module 704 may further be configured to parse data that is received from the medical image reading professionals who submit applications and store the information in a data repository or database.

A managed database module 706 may be configured to manage one or more data repositories or databases that are used to store contact and other information of medical image reading professionals, diagnoses databases, and any other databases that may be utilized in providing for the principles of the present invention. The module 706 may manage databases that are locally or remotely located from the server 502 (FIG. 5).

A managed medical images module 708 may be configured to manage medical images in combination or separately from the managed database module 706. The managed medical images module 708 may be configured to manage the medical images themselves, device information used to collect the images, names of technicians used to collect the medical images, and any other information that may be of benefit to the medical image reading professionals or medical image reading professionals network manager.

A managed readings and billing module 710 may be configured to manage readings or diagnoses made by medical image reading professionals in response to reading medical images. The module 710 may be configured to associate diagnoses with medical images and patients. The module 710 may be further configured to manage billing by associating a medical image reading professional with his or her diagnoses so that the medical image reading professional is properly paid for performing the diagnoses.

An insurance payment submission module 712 may be configured to communicate with the managed readings and billing module 710 or other module(s) 700 so as to determine when medical image reading professionals perform readings and are due payment. If medical image reading professionals are due payment, then the insurance payment submission module 712 may be configured to be manually, semi-automatically, or automatically operated to submit an insurance payment request, such as insurance payment requests 540 of FIG. 5, to an insurance company for payment.

A determine rating parameter(s) module 714 may be configured to determine at least one rating parameter for a medical image reading professional. In one embodiment, the module 714 may be configured to present a graphical user interface that enables entry of information associated with patient outcomes based on readings and diagnoses made by a medical image reading professional. The graphical user interface may enable a user to access medical insurance claims and enter information associated therewith, access medical treatment plans and enter information associated therewith, and/or access and enter other information associated with patients of which the medical image reading professional has diagnosed. Alternatively, the module 714 may be automated and collect the patient treatment and outcome information as it is generated and available on one or more computer systems or databases.

Figure 7B:
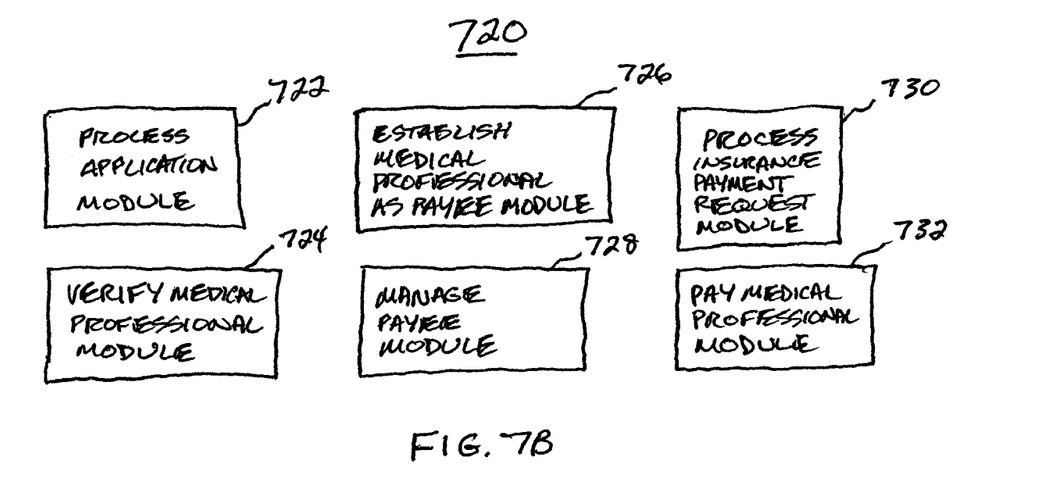
FIG. 7B is a block diagram of an illustrative set of modules configured to process information to enable an insurance company to manage medical image reading professionals and payment thereto.

FIG. 7B is a block diagram of an illustrative set of modules 720 configured to process information to enable an insurance company to manage medical professionals and payment thereto. The modules 720 may be part of the software 530 (FIG. 5). The modules 720 may include a process application module 722 that is configured to process an application of a medical professional, such as a medical image reading professional, that is a member of a medical image reading professionals network. The process application module 722 may be configured to receive an electronically filed application or receive input from someone entering information submitted on a paper application to become a registered payee of the insurance company.

A verify medical professional module 724 may be configured to verify that medical professionals who submit applications to become registered payees of the insurance company are, in fact, members of a medical image reading professionals network. The module 724 may be configured to communicate a query to a medical image reading professionals network server and/or database to determine whether a medical professional is registered with the medical image reading professionals network. The module 724 may further be configured to receive a response back for processing and storage.

An establish medical professional as payee module may be configured to determine if the response received by the verify medical professional module 724 was positive, and, if so, then the insurance company may recognize the medical professional as a payee. If an insurance payment request is made by the medical professional or medical image reading professionals network manager with the medical professional as the person who performed medical image reading services, then the insurance company can pay the services bill.

A manage payee module 728 may be configured to manage a database of payees. In one embodiment, the manage payee module 728 may be configured to receive communications from a medical image reading professionals network manager indicating that a medical professional is no longer a member and alter the payee status.

A process insurance payment request module 730 may be configured to process insurance payment requests. In one embodiment, the module 730 may be configured to receive information identifying a medical professional, determine that the medical professional is a registered payee, optionally verify with the medical image reading professionals network manager that the medical professional is in good standing, verify that the medical professional is reading medical images that are within his or her expertise, determine at least one rating parameter of the medical image reading professional, and so on.

A pay medical professional module 732 may be configured to receive a pay request to pay the medical professional who performed medical image reading services and initiate payment to the medical professional. In one embodiment, the payment may be an electronic payment, such as direct deposit, or paper payment, such as via a check. The payment may be made by the insurance company or by an agent of the insurance company.

Figure 8:
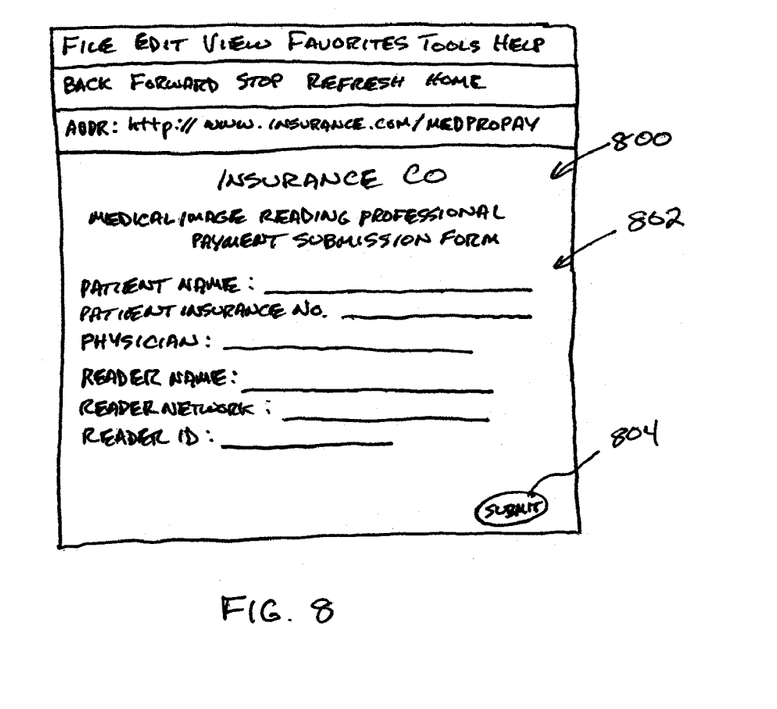
FIG. 8 is an illustration of an illustrative graphical user interface that enables an insurance payment form to be submitted by a medical image reading professional.

FIG. 8 is an illustration of an illustrative graphical user interface 800, such as a webpage, that enables an insurance payment form to be submitted by a medical image reading professional. The insurance payment form may include patient name, patient insurance number, attending physician, medical image reading professional's name or reader name, reader network, reader ID, and any other information that the insurance company may utilize in determining how much the medical image reading professional or medical image reading professional network manager is to be paid for services rendered by the medical image reading professional. The webpage 800 may be automatically filled in by the insurance payment submission module 712 (FIG. 7A) or manually by a user at the medical image reading professionals network. Alternatively, the medical image reading professional may submit the insurance payment form. Once the requested information is entered into text entry fields 802, the user may select a "submit" soft-button 804 for the information to be communicated to a server, such as server 526 (FIG. 5), operated by an insurance company. The insurance company server 526 may execute software 530 that is configured to receive the information entered into the payment submission form and verify that the medical image reading professional is part of a medical image reading professionals network so as to process the payment information and provide payment in accordance with a contract between the insurance company and medical image reading professionals network or medical image reading professional.

The previous detailed description of a small number of embodiments for implementing the invention is not intended to be limiting in scope. One of skill in this art will immediately envisage the methods and variations used to implement this invention in other areas than those described in detail. The following claims set forth a number of the embodiments of the invention disclosed with greater particularity.

What is claimed:

1. A method for an insurance company to contract with medical image reading professionals, said method comprising:

receiving, by a computing system of the insurance company, an application of a medical image reading professional who, to perform medical duties, receives medical information from a medical professional network manager and who has qualified to participate in a network of medical image reading professionals that the medical professional network manager manages, the medical image reading professional being identified as an expert in reading medical images of one or more anatomical regions, the medical professional network manager further having an agreement with the insurance company to identify to the insurance company an anatomical region captured in medical images read by medical image reading professionals in the network of medical image reading professionals;

verifying, by the computing system, that the medical image reading professional is a member of the network of medical image reading professionals;

approving, by the computing system, the application of the medical image reading professional in response to positively verifying that the medical image reading professional is a member of the network;

establishing, by the computing system, the medical image reading professional as a payee in performing medical services;

in response to the insurance company receiving a claim for payment to the medical image reading professional for reading a medical image of an identified anatomical region, verifying that the medical image reading professional is an expert in reading medical images of the identified anatomical region;

making payment of the claim if the medical image reading professional is verified to be an expert in reading medical images of the identified anatomical region; and otherwise, denying payment on the claim.

2. The method according to claim 1, wherein receiving the application includes receiving the application from the medical image reading professional.

3. The method according to claim 1, wherein receiving the application includes receiving an area of expertise in which the medical image reading professional practices.

4. The method according to claim 1, wherein the medical professional network manager is independent of medical care facilities.

5. The method according to claim 1, further comprising:
evaluating the medical professional network manager; and
approving the medical professional network manager as an authorized service provider such that medical image reading professionals associated with the medical professional network manager are able to submit applications.

6. A system for paying medical image reading professionals, said system comprising:
a storage unit configured to store information; and
a processing unit in communication with said storage unit, and configured to execute:
a first module configured to recognize a network of medical image reading professionals who interpret medical information of patients to qualify for medical insurance payment reimbursement, each medical image reading professional in the network managed by a medical professional network manager having at least one rating parameter associated therewith indicative of outcome of patients who were treated based on assessments of medical conditions by a respective medical image reading professional, each of the medical image reading professionals being identified as an expert in reading medical images of one or more anatomical regions, the medical professional network manager further having an agreement with an insurance company to provide an identification of an anatomical region captured in medical images read by the medical image reading professionals in the network of medical image reading professionals, information representative of each medical image reading professional and the at least one rating parameter being stored in said storage; and a second module in communication with said first module, and configured to process insurance payment requests presented to the insurance company for the medical image reading professionals, the processing of the insurance payment requests including verifying that the medical image reading professional is an expert in reading medical images of the identified anatomical region; and a third module configured to (i) cause payment to be made to the medical image reading professional in the network in response to verifying that the medical image reading professional is an expert in reading medical images of the identified anatomical region or (ii) cause payment to be denied.

7. The system according to claim 6, further comprising:
a fourth module configured to process an application of a medical image reading professional to become a payee of the insurance company; and
a fifth module configured to establish the medical image reading professional as a payee.

8. The system according to claim 6, where said first and second modules are executed on a first server configured to communicate with a second server that maintains records of medical image reading professionals in the network of medical image reading professionals.

9. A method for paying medical image reading professionals, said method comprising:
recognizing, by a computing system, a network of medical image reading professionals who interpret medical information of patients to qualify for medical insurance payment reimbursement, each medical image reading professional in the network having at least one rating parameter associated therewith indicative of outcome of patients who were treated based on assessments of medical conditions by the respective medical image reading professional, each medical image reading professional being identified as an expert in reading medical images of one or more anatomical regions, the medical professional network manager of the medical image reading professionals network further having an agreement with an insurance company to provide an insurance company with an identification of an anatomical region captured in medical images read by the medical image reading professionals in the network of medical image reading professionals;

receiving, by the insurance company, an identification of the anatomical region captured in a medical image read by a medical image reading professional;

in response to verifying that the medical image reading professional who performed the reading of the medical images is an expert in reading medical images of the identified anatomical region by the insurance company, paying the medical image reading professional in the network of medical image reading professionals for reading the medical image of an anatomical region; and otherwise, denying payment to the medical image reading professional.

10. The method according to claim 9, further comprising paying referring medical professionals who refer the patients to a medical image reading professional in the network of medical image reading professionals.

11. The method according to claim 10, wherein paying the referring medical professionals includes paying the referring medical professionals different from referring medical professionals who refer the patients to a medical image reading professional not in the network of medical image reading professionals.

12. The method according to claim 9, wherein recognizing a network of medical image reading professionals includes recognizing a network of medical image reading professionals who are experts in reading medical images of anatomical regions as a result of reading a certain minimum number of medical images of the identified anatomical regions over a given time frame.

13. A method of paying medical image reading professionals for performing services, said method comprising:
   receiving, by the computing system, a medical insurance claim for medical services having been performed on a patient with a medical condition of an anatomical region, the medical insurance claim indicating medical image reading services having been rendered by a medical image reading professional;
   receiving, by the computing system, an identification of a medical image reading professional who performed the medical image reading services, the medical image reading professional being identified as an expert in reading medical images of the anatomical region;
   confirming, by the computing system, that the medical image reading professional is an expert in reading medical images of the anatomical region of which the patient has a medical condition, and, pursuant to an agreement between an insurance company and medical professional network manager, an identification of the anatomical region of the medical images being provided to the insurance company for the confirmation;
   receiving, by the insurance company, an identification of the anatomical region captured in a medical image read by a medical image reading professional;
   in response to verifying that the medical image reading professional is an expert in reading medical images of the identified anatomical region, paying the medical image reading professional for performing the medical image reading services; and
   otherwise, not paying the medical image reading professional.

14. The method according to claim 13, wherein the medical image reading professional is in a network of medical image reading professionals that is independent of a medical facility.

15. The method according to claim 14, further comprising:
   receiving a medical claim for medical service from a treating physician, the treating physician having referred the patient to a medical image reading professional outside the network; and
   paying the treating physician a different amount than had the treating physician referred the patient to the medical image reading professional in the network of medical image reading professionals.

* * * * *